United States Patent [19]

Vich

[11] Patent Number: 4,877,020

[45] Date of Patent: Oct. 31, 1989

[54] APPARATUS FOR BONE GRAFT

[76] Inventor: Jose M. O. Vich, Av. de Montero Rios 24, 3º, Vigo (Pontevedra), Spain

[21] Appl. No.: 198,081

[22] Filed: May 24, 1988

Related U.S. Application Data

[62] Division of Ser. No. 707,305, Mar. 1, 1985.

[30] Foreign Application Priority Data

Nov. 30, 1984 [ES] Spain ..................... 283078

[51] Int. Cl.$^4$ ........................ A61F 5/04; A61B 17/00; B25B 23/00
[52] U.S. Cl. ............................. 128/92 V; 128/303 R; 81/443
[58] Field of Search ............... 128/92 V; 81/443, 444, 81/445, 446, 447, 450

[56] References Cited

U.S. PATENT DOCUMENTS

| | | | |
|---|---|---|---|
| 1,058,454 | 4/1913 | Moores | 81/444 |
| 2,248,054 | 7/1941 | Becker | 128/92 V |
| 2,312,869 | 3/1943 | Boyer | 128/92 V |
| 2,406,952 | 9/1946 | Josepho | 81/450 |
| 2,532,972 | 12/1950 | Vertin | 128/92 V |
| 2,579,438 | 12/1951 | Longfellow | 128/92 V |
| 3,311,002 | 3/1967 | Hoose | 81/447 |
| 3,604,487 | 9/1971 | Gilbert | 128/92 V |

FOREIGN PATENT DOCUMENTS 411233 2/1927 Fed. Rep. of Germany ........ 81/444

Primary Examiner—Richard J. Apley
Assistant Examiner—David J. Isabella
Attorney, Agent, or Firm—Flynn, Thiel, Boutell & Tanis

[57] ABSTRACT

An instrument for inserting a bone graft, wherein the bone graft is of a substantially cylindrical configuration and is extremely threaded. The graft is clampingly held at one end of an elongated instrument which securely holds the graft and permits it to be threadably inserted into a previously prepared intervertebral bed. After the graft has been properly inserted into the bed, the instrument can be manually released from the graft.

The instrument for inserting the graft includes an elongated handle, and a control rod extends coaxially through the handle and is rotatably and threadably coupled thereto. The control rod at the lower end thereof has a part which projects outwardly from the handle and releasably grippingly engages the implant.

1 Claim, 2 Drawing Sheets

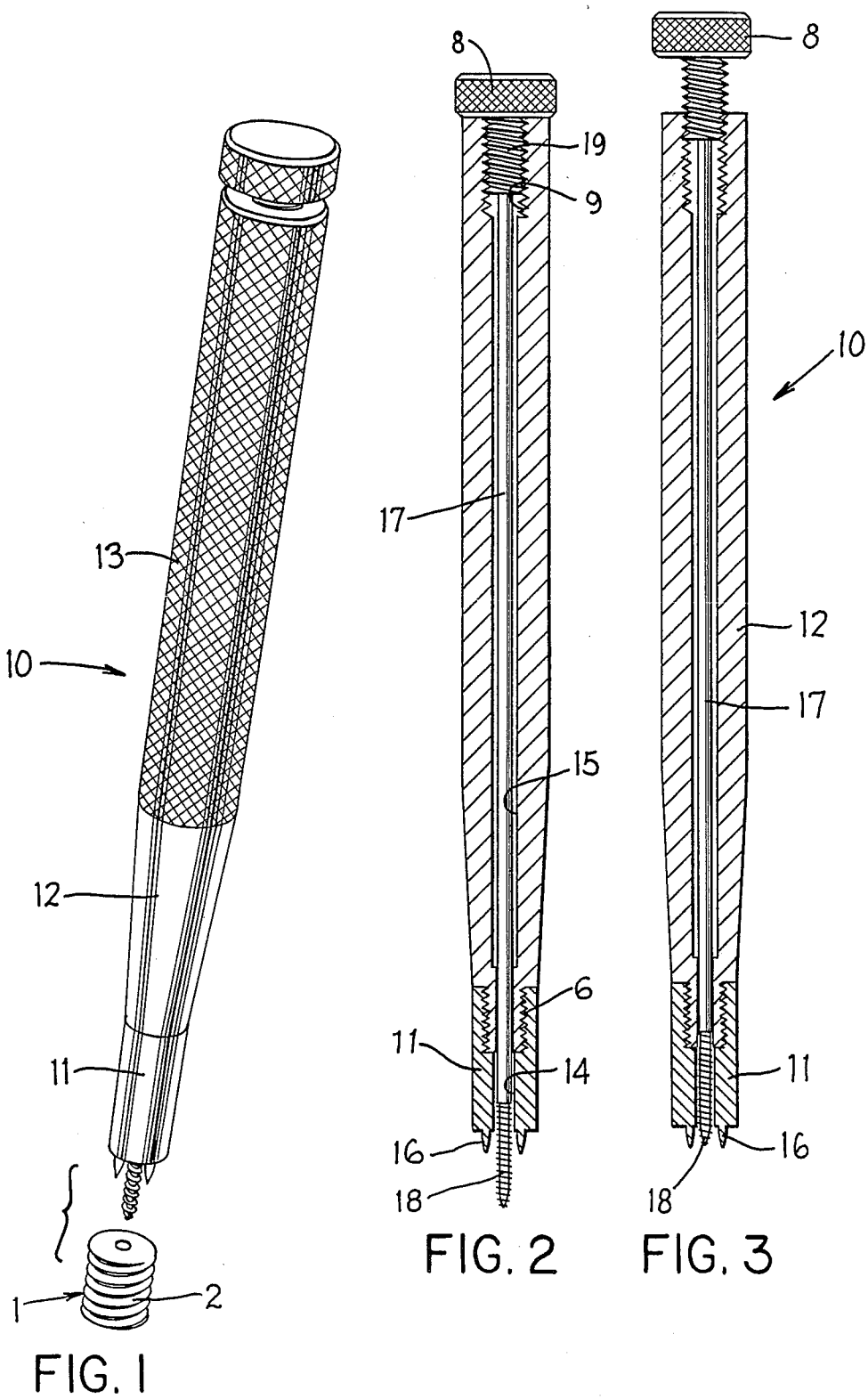

APPARATUS FOR BONE GRAFT

This is a division of Ser. No. 707,305, filed Mar. 1, 1985, presently pending.

FIELD OF THE INVENTION

This invention relates to improved surgical instruments for inserting an Osseous Graft.

BACKGROUND OF THE INVENTION

Since Smith-Robinson, Derrymaker and Cloward published in the middle fifties their works (which they carried out simultaneously but independently) describing their respective surgical methods to execute the intersomatic arthrodesis of the cervical segment, very few technical variations have been brought about over the last 30 years, which was undoubtedly due to the obvious advantages of their methods over former techniques: their relatively easy execution, the few risks involved and the excellent results obtained.

Considering that the technique by Cloward (Anterior Intersomatic Arthrodesis with Cylindrical Graft) is the most widely used, not only at out Hospital but also at a large number of traumatology and neurosurgery services all over the world, we started a clinical and experimental work on the basis of our own experience with this technique, which covers the management of nearly 300 patients operated over the last eight years. In this sense, a series of changes was introduced affecting both the graft and some of the elements of Cloward's basic instruments, which changes permit minimization or elimination of a considerable number of intraoperatory and postsurgical complications which are frequently mentioned in the medical literature.

Our contribution to this surgical technique is summarized in two main points:

(a) the substitution of the plain cylindrical graft to be implanted in the corresponding intersomatic space, by a graft provided with a thread or coil, and (b) the design of two instruments required to carry out the helicoidal insertion of the graft.

The technical procedure is schematically described as follows: after obtaining the graft (either by autologous extraction of the patient's own iliac crest or by the use of either a homologous graft or a kielsurgibone heterologous graft) a coil is threaded intrasurgically on the graft with a small lathe designed ad-hoc and previously sterilized, which permits the execution of the thread in a very easy and quick manner, with grooves which can be made as deep as required. In the case of heterologous grafts, the coil should preferably be threaded during the process of obtaining the graft.

The resulting helicoidal graft is kept in highly sterilized condition while the anterior side of the vertebral cervical bodies is being prepared following Cloward's standard technique.

After the cylindrical bed as been drilled in the corresponding intervertebral space, the graft is helicoidally inserted with the instruments specially designed for the purpose.

In order to facilitate the comprehension of all explanations, two sheets with drawings are attached to this descriptive memorandum, illustrating two examples of applications, wherein:

BRIEF DESCRIPTION OF DRAWINGS

FIG. 1 is a perspective view illustrating a first instrument used for inserting the graft.

FIGS. 2 and 3 are central sectional views illustrating the instrument of FIG. 1 in two positions of use.

DETAILED DESCRIPTION

Figures 4, 5, 6:
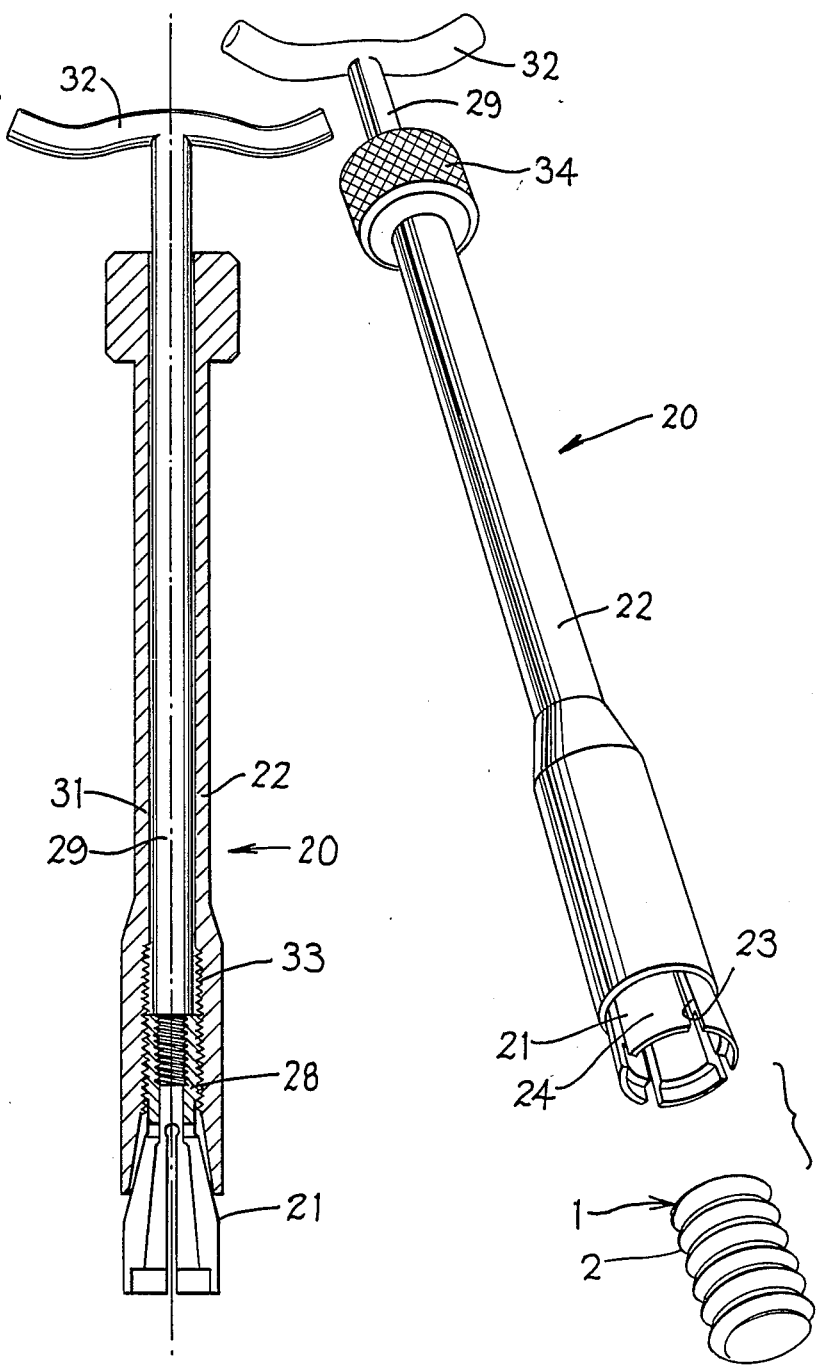
FIG. 4 is a perspective view similar to FIG. 1 but illustrating a second instrument for handling and inserting the graft.
FIGS. 5 and 6 are central sectional views illustrating the instrument of FIG. 4 in two different positions of use.

Referring to the drawings, an osseous graft 1 is illustrated which may be either autologous, homologous or heterologous, and having the particular feature of being provided with a helicoidal thread therearound, with a depth of groove which may be varied as required.

For the insertion of the helicoidal graft 1 into the bed previously drilled in the intervertebral space, two devices or instruments have been designed, which firmly holding the graft in one end, and act as handles to enable the manipulation of the graft during the process of implantation.

In the instrument 10 of FIGS. 1-3, the graft 1 is screwed to the apparatus holding head. In the case of the second instrument 20 of FIGS. 4-6 (which is to be used when the graft's structure makes it advisable), the graft is held on the holding head by means of claws or clamps which externally embrace a portion of the end of the graft.

Concerning more specifically the instrument 10 of FIGS. 1-3, it includes a substantially cylindrical sleeve-like holding head 11 which is secured to one end of an elongated rodlike handle 12, the latter having at least the upper portion of the periphery thereof serrated or roughened at 13 to facilitate gripping thereof. The head 11 is interchangeably attached to the handle, as by a threaded connection 6, so that the head can be interchanged to permit selection of a head having a diameter or size corresponding to the diameter of the graft. This head 11 has a central opening 14 extending coaxially therethrough and aligned with a further opening or bore 15 which extends coaxially through the handle 12. Head 11, at the lower or frontal end thereof, has two small but elongated pins 16 projecting axially outwardly therefrom, which pins taper to a point and are disposed closely adjacent the bore 14 on substantially diametrically opposite sides thereof. An elongated rod 17 extends through and is rotatable relative to the aligned bores 14-15, which rod 17 at the lower end thereof is provided with a projecting threaded portion or screw 18 which projects through the holding head 11. Rod 17, at the upper end thereof, has a threaded part 19 of enlarged diameter which is threadably engaged with a threaded bore 9 which is formed in and opens coaxially upwardly through the upper end of the handle 12. An enlarged gripping knob 8 is fixedly secured to the upper end of this rod 17 and is positioned adjacent the upper free end of the handle 12 so as to be readily accessible.

In use of the instrument 10, the rod 17 is initially maintained in the retracted position of FIG. 3. The implant is pushed against the lower end of the head 11 so that the lower projecting end of the screw 18 initially pilots into the small central opening formed in the graft, and at the same time the pins 16 axially penetrate the graft to securely hold it nonrotatable with respect to the holding head. By gripping and rotating the knob 8 relative to handle 12, this hence causes rotation of rod 17 so that screw 18 rotates and projects axially outwardly from the head so as to threadably engage and hence securely hold the graft 1. With the graft securely held on the head of the instrument, the graft can then be inserted into the previously prepared bed by effecting rotation of the instrument substantially about its longitudinal axis, which in turn rotates the graft and enables it to be threadably screwed into the interverbetral bed. Thereafter the knob 8 and rod 17 are gripped and manually rotated relative to handle 12 in the opposite rotational direction so as to unscrew the screw 18 from the implant so that the instrument again essentially assumes the position illustrated by FIG. 3. Once this screw 18 has been unscrewed from the implant, then the pins 16 are freed from the graft by gently moving the instrument, such as a gentle rocking sideward back-and-forth rocking movement, substantially in the plane containing the two pins.

Concerning now the second instrument 20 of FIGS. 4-6, same again includes an elongated rodlike handle 22 having a head 21 replacably attached to the lower end thereof. The head 21, in this embodiment, includes a sleeve portion which has a plurality of circumferentially spaced cuts or slits 23 projecting axially inwardly from the lower free end thereof so that there is hence defined a plurality of resilient clamping jaws or pads 24, is structure hence resembling that of a collet. This holding head, at the lower free end thereof, has a bore 25 formed therein which terminates in a shoulder and which is sized to accommodate one end of the implant 1. This holding head, at least the sleeve portion provided with the slits 23 therein, has an external tapered surface 26 which is received within a bore 27 formed in the lower end of handle 22, which bore 27 is of a diverging tapered configuration as it opens outwardly so as to effect a wedging and hence clamping of the head 21 around the graft 1. Head 21 has a hub 28 which is fixedly secured to the lower end of an elongated rod 29, the latter projecting coaxially through a bore 31 which extends coaxially through the handle 22 and terminates in the conical opening 27. This rod 29 projects outwardly through the upper end of the handle and itself is provided with a T-shaped gripping head 32. The lower end of bore 31 is internally threaded at 33 and is threadably engaged with corresponding external threads formed on the hub 28. Handle 22 preferably has an enlarged and substantially cylindrical gripping knob 34 at the upper end, the latter preferably being externally knurled or roughened.

In use of the instrument 20, the graft is initially inserted into the bore 25 of the holding head 21 when the latter is in the position of FIG. 5. Rod 29 and holding head 21 are then rotated relative to handle 22 which causes the head 21 to be axially retracted toward the position of FIG. 6, whereupon the tapered surfaces 26 and 27 wedgingly cooperate so that the collet structure 24 is circumferentially elastically deformed to compressingly and hence securely hold the one end of the graft 1. The implant 1 is then inserted into the intervertebral bed by helicoidally threading the graft into the bed by effecting rotation of the instrument accompanied by a slight axial displacement thereof. After the implant has been completed, then portion 32 and knob 34 are independently gripped and the handle 22 is manually rotated relative to the rod 29 so as to effect axial withdrawal of the handle 22 upwardly relative to the rod, thereby releasing the holding portion 21 from the conical surface 27. The holding portion 21 thus resiliently expands and releases the graft 1, thereby leaving the graft securing screwed into the bed.

The advantages which the use of the graft object of the invention presents as compared to the standard technique, can be summarized as follows:

1. The gentleness in which the helicoidal graft is inserted avoids:

(a) the unleashing of spinal cord contusions due to the repeated and at times rough impact of the hammer striking directly on the base of the graft. This serious neurological complication would be aggravated on patients with myelopathies, where an associated spinal cord fragility would be associated. Insofar as this is concerned, although the bibliography and our personal experiences are fortunately scarce, some cases of the traparesis, breathing irregularities and even exitus after the repeated and indiscriminated traumatism on the front of the corresponding medullar segment have been reported.

(b) Breakage of the graft due to the impact of the hammer.

(c) The possibility of the graft invading the spinal cord channel may also be avoided, because the depth of introduction of the graft into the receiving bed can be perfectly calculated, which is not the case when the classical method is being used, as it is always difficult to evaluate the impact of the hammer, with catastrophical consequences as it can be easily understood.

2. The possibility of perfectly calculating the depth of insertion of the graft permits its introduction up to the very free rim on the back of the vertebral bodies, which will contribute to prevent the lowering of the intervertebral space and secondary angulations.

3. Should any intra or post-operatory complications ever appear (haematoma, spinal cord compression, breathing alterations, etc.) the extraction of the graft can be easily carried out.

4. Owing to the fact that the helicoidal method permits the insertion of grafts with wider diameters than the one of the receiving bed, a steadier fixing into the intervertebral space will be obtained, because both elements (thread and diameter) will help increase the strength of the arthrodesis and consequently sliding will be more difficult.

5. Although for the time being no patients suffering from cervical fracture luxation have been operated by us, on extensive studies carried out on cadavers with cervical columns intentionally luxated, the helicoidal graft turned out to be clearly superior to the plain one, for the fixing of the injured space.

The process, within its limits, can be carried out in other executions which differ in detail from those mentioned herein in the way of examples and which will likewise be protected by the registration requested.

The embodiments of the invention in which an exclusive property or privilege is claimed are defined as follows:

1. An instrument for holding and permitting insertion of a substantially cylindrical bone implant which is externally threaded into a substantially cylindrical bed, said instrument comprising:
   an elongated rod shaped handle defining opposite ends and having a substantially central bore extending coaxially therethrough, one end of said handle defining an opening terminating in a substantially frusto-conical bore which divergently opens outwardly through said one end of the handle;

a substantially cylindrical sleevelike implant holding head engageable with said one end of said handle, said holding head being formed of a sleeve defining a bore for accommodating one end of the implant, said sleeve having axial slits formed in one end thereof so that the sleeve defines a resiliently deformable collet structure for gripping the implant, said sleeve having an external frusto-conical surface which projects into and wedgingly engages the frusto-conical surface on said handle;

an elongated control rod projecting coaxially through the opening of said handle and being fixedly secured to said holding head, said control rod projecting outwardly through the other end of said handle and being provided with an enlarged gripping portion thereon; and said control rod and said handle each having a coaxially threaded portion to be threadably coupled together so that relative rotation therebetween results in a corresponding axial displacement of the holding head.

* * * * *